United States Patent [19]
Chiang et al.

[11] Patent Number: 5,886,243
[45] Date of Patent: Mar. 23, 1999

[54] GENETIC ENGINEERING OF WOOD COLOR IN PLANTS

[75] Inventors: Vincent Lee C. Chiang; Chung Jui Tsai, both of Hancock; Gopi K. Podila, Houghton, all of Mich.

[73] Assignee: Board of Control of Michigan Technological University, Houghton, Mich.

[21] Appl. No.: 715,325

[22] Filed: Sep. 18, 1996

Related U.S. Application Data

[60] Provisional application No. 60/007,727 Nov. 30, 1995.

[51] Int. Cl.$^6$ .......................... C12N 15/29; C12N 15/82; A01H 5/00; A01H 4/00
[52] U.S. Cl. .................................. 800/205; 800/DIG. 48; 435/172.3; 435/320.1; 435/419; 536/23.6; 536/24.1
[58] Field of Search .............................. 800/205, DIG. 8; 435/172.3, 320.1, 419; 536/23.6, 24.1

[56] References Cited

U.S. PATENT DOCUMENTS

| 4,795,855 | 1/1989 | Fillatti et al. ............................... 800/1 |
| 5,451,514 | 9/1995 | Boudet et al. ........................ 435/172.3 |

FOREIGN PATENT DOCUMENTS

| 2005597 | 6/1990 | Canada ........................... C12N 15/00 |
| WO 93/05160 | 3/1993 | WIPO ............................. C12N 15/54 |

*Primary Examiner*—Douglas W. Robinson
*Assistant Examiner*—Thomas Haas
*Attorney, Agent, or Firm*—Michael Best & Friedrich LLP

[57] ABSTRACT

The invention relates to genetically engineering the wood color of woody plants by incorporation of the lignin pathway gene O-methyltransferase into the genome of the plants.

30 Claims, 1 Drawing Sheet

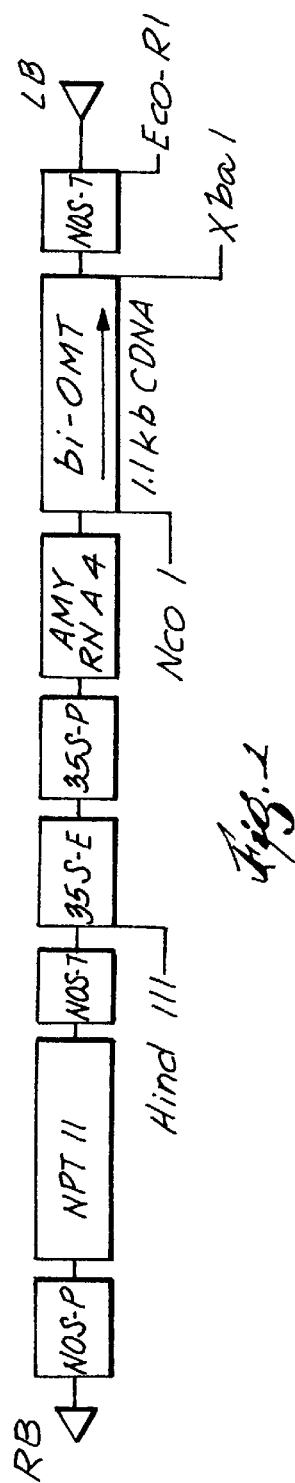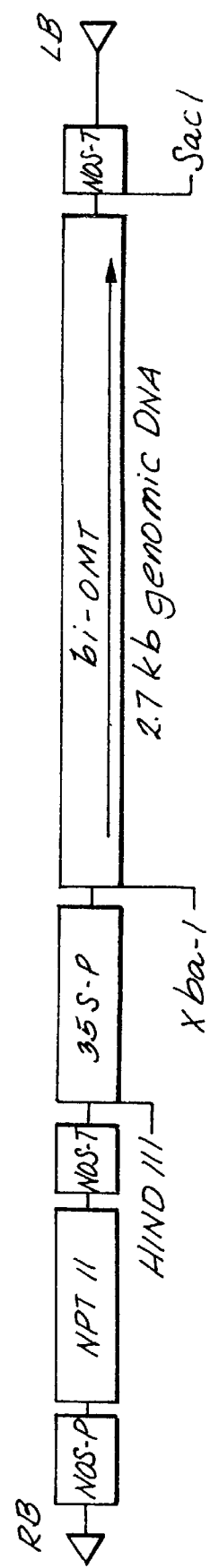

GENETIC ENGINEERING OF WOOD COLOR IN PLANTS

RELATED APPLICATION

This application claims the benefit of prior filed, copending provisional application Ser. No. 60/007727 filed Nov. 30, 1995 entitled "GENETIC MODIFICATION OF ANGIOSPERM PULPWOOD SPECIES".

FIELD OF THE INVENTION

The invention relates to genetically modifying the wood color of woody plants, and more particularly, to genetically modifying the wood color of woody plants through the genetic manipulation of a lignin pathway gene such as O-methyltransferase.

BACKGROUND OF THE INVENTION

Genetic engineering of forest tree species to conform to desired traits has shifted the emphasis in forest tree improvement away from the traditional breeding programs during the past decade. Although research on genetic engineering of forest trees has been vigorous, the progress has been slow due.

Very little progress has been reported regarding the genetic engineering of color in plant species. The ability to genetically alter the color of plants would be of great value to industries such as the furniture industry to make furniture from genetically modified wood or to the paper industry. Accordingly, these exists a need for such genetic color modification of plant species.

Further, there is a need for improving the efficiency of pulping of wood. Considerable monetary and environmental costs are incurred by the paper industry in removing lignin from cellulose during the production of wood pulp and paper.

SUMMARY OF THE INVENTION

The invention provides a method to genetically alter the wood color of woody plants using the lignin pathway gene O-methyltransferase. The genetically altered color creates unique grain patterns in wood. Due to the genetic modification using a lignin pathway gene, the genetically altered woody plant also has an altered lignin structure making processing such as pulping easier and more energy efficient.

It is one object of the present invention to provide a method to genetically alter the wood color of woody plants.

It is another object of the present invention to provide a method to genetically alter the natural color of wood through the manipulation of a lignin pathway gene.

It is another object of the present invention to provide a method to both genetically alter the color of wood as well as genetically alter the structure of the lignin in that wood.

It is another object of the present invention to genetically alter the color of the wood of plants from the genus Populus.

Other features and advantages of the invention will become apparent to those of ordinary skill in the art upon review of the following detailed description, claims, and drawings.

BRIEF DESCRIPTION OF THE DRAWINGS

FIG. 1 is a diagram of construct pFOMT1 which contains a 1.1 kb bi-OMT cDNA sense fragment with the whole coding region between 35S enhancer-promoter/AMV RNA4 and NOS terminator; and FIG. 2 is a diagram of construct pFOMT2 which contains a 2.7 kb genomic bi-OMT full-length DNA in the sense orientation between 35S promoter and NOS terminator.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE PREFERRED EMBODIMENT

The color of woody plant species can be modified by transformation with a lignin pathway gene and specifically the lignin pathway gene that codes for the enzyme O-methyltransferase (OMT).

The O-methyltransferase enzyme of gymnosperms and angiosperms differ in substrate specificity for caffeic acid, with gymnosperms being monospecific for caffeic acid and angiosperms being bispecific, catalyzing the methylation of both caffeic acid and 5-hydroxyferulic acid. Gymnosperm lignin also termed guaiacyl lignin is composed mainly of one precursor (coniferyl alcohol) whereas angiosperm lignin also termed guaiacyl-syringyl lignin is formed from the polymerization of two main precursors (coniferyl alcohol and sinapyl alcohol). The ratio of syringyl to guaiacyl units is directly related to the efficiency of kraft delignification, with higher syringyl quantities improving the efficiency. Softwoods largely synthesize coniferyl alcohol and form a lignin which is virtually completely made up of guaiacyl units. Hardwoods synthesize both coniferyl and sinapyl alcohols forming less condensed lignin of guaiacyl/syringyl mixtures in various proportions. The ratio of syringyl to guaiacyl units is directly related to the efficiency of kraft pulping, as the lignin found in angiospermous trees is less condensed than the lignin in gymnospermous trees, and is therefore more easily separated from the wood's cellulose in the pulping process. The sinapyl alcohol precursor of syringyl lignin is absent in softwoods, due to a deficiency of two key enzymes in the phenylpropranoid pathway; bi-specific O-methyltransferase and ferulic acid 5-hydroxylase.

The OMT enzyme has been studied in many plants some of which include Japanese black pine, shoots of bamboo, ginkgo, poplar, tobacco, spinach beet, soybean, parley, alfalfa root nodules, eucalyptus and aspen.

Generally, the wood color of woody plant species can be altered by genetic transformation with a homologous OMT gene in the sense orientation. The description of the invention below refers to aspen (*Populus tremuloides*) when necessary for the sake of example. However, it should be noted that the invention is not limited to the modification of the wood color in aspen. The method of the present invention is capable of being practiced for other woody plant species using an homologous OMT gene.

A. OMT Gene

The present invention utilizes a homologous OMT gene to genetically alter the wood color of woody plants. The invention as described below utilizes a cDNA clone of the OMT gene. However, it should be noted that genomic DNA can also be utilized in the present invention.

Purified and isolated OMT DNA can be obtained using a cDNA cloning method such as set forth below and in Bugos et al., Plant Mol. Bio. 17:1203–1215 (1991) which is incorporated herein by reference. A cDNA clone encoding OMT is isolated by immunological screening of a λgt11 expression library prepared from poly(A)+ RNA of developing secondary xylem as follows.

The differentiating xylem of the species is obtained. Total RNA is extracted from the developing secondary xylem. See for example Logemann et al., Anal. Biochem 163:16–20 (1987). 5M guanidine hydrochloride is used in order to reduce starch gelatinization. The RNA is further purified by precipitation with 2.5M LiCl. See for example Okita et al., Plant Physiol. 69:834–839 (1982). Poly(A)$^+$ RNA is isolated using Hybond-mAP paper. From the poly(A)$^+$ RNA, double-stranded cDNA is prepared using a library construction system from Invitrogen Corporation, San Diego, Calif. See for example Sambrook et al., Molecular Cloning, 2nd ed., Cold Spring Harbor Laboratory Press, Cold Spring Harbor (1989). The double stranded cDNA is ligated to linkers and then cloned into a vector, for example to EcoR1-Not1 linkers and then into the EcoR1 site of λgt11 (Strategene Cloning Systems, La Jolla, Calif.).

The vector is then used to transform or transfect a host cell. With λgt11, the insert-containing lambda vectors are packaged with lambda proteins and infected into *Escherichia coli* such as strain Y1090. See for example Mierendorf et al., Methods In Enzymol. 152:458–569 (1987).

The cDNA library thus prepared can be screened in any suitable manner. In a preferred embodiment, the host cells are transformed or transfected in a manner allowing the host cell to express the polypeptide of the DNA inserted into the vector. This can be done by utilizing a vector having DNA sequences flanking the insertion area with one or more codons preferred for expression in *E. coli* cells. In such a case, the host cells themselves, or extracts of the host cells, can be screened with antibodies against the OMT enzyme.

The OMT enzyme used to prepare antibodies is purified from xylem using a combination of purification techniques as set forth in Bugos et al., Phytochemistry 31:5:1495–1498 (1992). The OMT enzyme is isolated from differentiating xylem and is then purified such as 180-fold by a process using DEAE-cellulose chromatography, HPLC gel filtration and affinity chromatography on S-adenosyl-L-homocysteine agarose. Using denaturing polyacrylamide gel electrophoresis (SDS-PAGE), one protein band with a molecular weight of 45,000 daltons is observed. The purified OMT enzyme catalyzes the methylation of both 5-hydroxyferulic acid and caffeic acid, with an activity ratio of 3.1:1. S-adenosyl-L-homocysteine is an effective inhibitor of the enzyme.

Using the purified enzyme, rabbit antibodies to the OMT enzyme can be produced in a conventional manner. Bugos et al., Phytochemistry 31:5:1495–1498 (1992). The cDNA can then be screened with antibodies against the OMT enzyme. Clones can be detected by the antibodies as expressing OMT polypeptides. The DNA from the clones can then be isolated. The clones have an insert DNA of about 1.5 bp. After the putative, positive λgt11 clones are plaque purified. Insert DNA of a clone is excised with Not1 and sub-cloned into Bluescript II. See for example Sambrook et al., Molecular Cloning, 2d ed., Cold Spring Harbor Laboratory Press, Cold Spring Harbor (1989).

The nucleotide sequence can then be determined by the dideoxynucleotide method, for example Sanger et al., Proc. Natl. Acad. Sci. 74:5463–5467 (1977), using a T7 Sequencing Kit for the entire length of the clone in both directions. Subclones are prepared by excision with EcoR1, BamH1, XhoI and HincII and sequenced using primers complementary to sequences bordering the multiple cloning site of Bluescript II (Strategene Cloning Systems, La Jolla, Calif.). Synthetic oligonucleotide primers are used to verify overlap regions of restriction sites. An open-reading frame of 1095 bp encodes a polypeptide of 365 amino acid residues with a predicted molecular weight of 39,802 daltons which corresponds well with the size of the bispecific OMT subunit.

The nucleotide sequence of bispecific aspen OMT cDNA clone is set forth as SEQ ID NO:1. The nucleotide sequence of SEQ ID NO:1 is numbered beginning with the 5' end of the cDNA clone. SEQ ID NO:1 includes the amino acid sequence, in standard three letter designations, directly beneath the corresponding codons.

The deduced amino-acid sequence for aspen bispecific OMT is set forth as SEQ ID NO:2. The first methionine of the open reading frame of the amino acid sequence is designated as the first amino acid of the putative polypeptide.

Three internal peptides of purified aspen bispecific OMT sequenced by automated Edman degradation are identical to portions of SEQ ID NO:1. Since the amino terminus of aspen bispecific OMT is blocked, as determined by the automated Edman degradation, these three internal peptides were deduced by digesting the purified enzyme with *Staphylococcus aureus* endoproteinase Glu-C. The peptides were isolated by reverse-phase HPLC, and were sequenced by automated Edman degradation.

The polynucleotide code for the OMT enzyme was expressed as a protein in *E. coli*, as the Bluescript II vector has codons preferred for expression in *E. coli* cells. The OMT expressed from the Bluescript II vector in *E. coli* was found to have bispecific activities in approximately the same ratio as that of the natural enzyme. This expressed protein was also recognized by the antibodies for bispecific OMT enzyme.

The antibody for aspen bispecific OMT was also used to select an OMT clone from an alfalfa cDNA library, which was prepared from RNAs induced by a fungal elicitor, and 85% of the alfalfa OMT's predicted amino acid residues were found to be identical to that of the aspen bispecific OMT. This demonstrates a substantial amount of duplication in amino acid sequences encoding plant O-methyltransferases from diverse plant species.

The OMT gene has been isolated and sequenced in the following plant species: aspen, hybrid aspen, hybrid poplar, alfalfa, tobacco, prunus, zinnia and eucalyptus.

Comparisons have been made been at the nucleotide level between the nucleotide sequence of aspen OMT cDNA and that of other plant species. The percentage identity of OMT of various plant species is set forth below with accession numbers referring to the Gene Bank:

Hybrid poplar (*P.trichocarpa* x *deltoides*) OMT cDNA, accession #M73431, 97% identity;
Hybrid aspen (*P.Kitakamiensis*) OMT genomic DNA, accession #D49710, 97% identity (exons);
Hybrid aspen (*P.Kitakamiensis*) OMT genomic DNA, accession #D49711, 89% identity (exons);
Prunus (*Prunus amygdalus*) OMT cDNA, accession #X83217, 81% identity;
Eucalyptus (*Eucalyptus gunnii*) OMT cDNA, accession #X74814, 74% identity;
Alfalfa (*Medicago sativa*) OMT cDNA, accession #M63853, 77% identity;
Tobacco (*N.tabacum*) OMT1a cDNA, accession #X74452, 74% identity;
Tobacco (*N.tabacum*) OMT1b cDNA, accession #X74453, 75% identity;
Zinnia (*Zinnia elegans*) OMT cDNA, accession #U19911, 71% identity; and
*Chrysosplenium americannum* OMT cDNA, accession #U16793, 75% identity.

B. Transformation and Regeneration

Several methods for gene transformation of plant species with the OMT gene are available such as the use of a transformation vector, agroinfection, electroinjection, particle bombardment with a gene gun or microinjection. Preferably, a binary vector construct such as those set forth in FIGS. 1 and 2 is mobilized into a strain of Agrobacterium species. Preferably, Agrobacterium such as *tumefaciens* strain C58 is used as the DNA delivery system due to its efficiency and low cost. See Koncz, C. et al., Mol. Gen. Genet 204:383–396 (1986). The vectors are mobilized in *Agrobacterium tumefaciens* using the freeze-thaw method of Holstein et al., Mol. Gen. Genet. 163:181–187 (1978). The vectors are described in Tsai et al., Plant Cell Reports 14:94–97 (1994) which is hereby incorporated by reference. The constructs pFOMT1 and pFOMT2 are also available from Michigan Technological University, Houghton, Mich.

Explants of young leaves from cuttings of aspen are obtained by cutting leaf disks from the young leaves along the midrib of the leaves using a corkborer that is 7 mm in diameter. The explants are surface sterilized in 20% commercial bleach for 10 minutes followed by rinsing three times with sterile double-distilled water.

All of the culture media used in this method includes the basal medium of woody plant medium (WPM) as described in Lloyd et al., Proc. Int. Plant Prop. Soc. 30:421–437 (1980) and supplemented with 2% sucrose. 650 mg/L calcium gluconate and 500 mg/L MES are added as pH buffers as described in De Block, Plant Physiol. 93:1110–1116 (1990). All culture media is adjusted to pH 5.5 prior to the addition of 0.075% Difco Bacto Agar and then autoclaved at 121° C. and 15 psi for 20 minutes. Filter sterilized antibiotics are added to all culture media after autoclaving. All culture media are maintained at 23±1° C. in a growth chamber with 16 hour photoperiods (160 $\mu E \times m^{-2} \times S^{-1}$) except for callus induction (as will be described later) which is maintained in the dark.

The sterilized explants are then inoculated with the mobilized vector with an overnight-grown agrobacterial suspension containing 20 $\mu M$ acetosyringone. After cocultivation, the explants are washed in sterile distilled water containing 300 mg/L cefotaxime to decontaminate. The explants are blotted dry with sterile Whatman No. 1 filter paper and transferred onto callus induction medium containing 40 mg/L kanamycin for selection of transformed cells. The callus induction medium is the basal medium with the addition of 6-benzyladenine (BA) and 2,4-dichlorophenoxyacetic acid (2,4-D) at concentrations of 0.5 mg/L and 1 mg/L, respectively, to induce callus. Cefotaxime at 300 mg/L is added to kill Agrobacterium.

The kanamycin-resistant explants are then subcultured on fresh callus induction media every two weeks. Callus formation occurs after approximately four weeks. Formed callus are separated from the explant and subcultured periodically for further proliferation.

When the callus clumps reach approximately 3 mm in diameter, the callus clumps are transferred to shoot regeneration medium. The shoot regeneration medium is the basal medium containing 100 mg/L kanamycin, 0.5 mg/L thidiazuron (TDZ) as a plant growth regulator and cefotaxime at 300 mg/L to kill Agrobacterium. Shoots were regenerated about four weeks after callus is transferred to regeneration medium.

Accordingly, as soon as the shoots are regenerated, they are immediately transferred to hormone-free elongation medium containing 100 mg/L kanamycin and, whenever necessary, cefotaxime (300 mg/L), to promote elongation. Green and healthy shoots elongated to 2–3 cm in length are excised and planted separately in a hormone-free rooting medium containing 100 mg/L kanamycin. The efficient uptake of kanamycin by shoots during their rooting stage provides the most effective selection for positive transformants.

Transgenic plants are then transplanted into soil medium of vermiculite:peatmoss:perlite at 1:1:1 and grown in the greenhouse.

The above described transformation and regeneration protocol is readily adaptable to other woody species. Other published transformation and regeneration protocols for tree species include Danekar et al., Bio/Technology 5:587–590 (1987); McGranahan et al., Bio/Technology 6:800–804 (1988); McGranahan et al., Plant Cell Reports 8:512–616 (1990); Chen, phD Thesis, North Carolina State University, Raleigh, N.C. (1991); Sullivan et al., Plant Cell Reports 12:303–306 (1993); Huang et al., In Vitro Cell Dev. Bio. 4:201–207 (1991); Wilde et al., Plant Physiol. 98:114–120 (1992); Minocha et al., 1986 Proc. TAPPI Research and Development Conference, TAPPI Press, Atlanta, pp. 89–91 (1986); Parsons et al., Bio/Technology 4:533–536 (1986); Fillatti et al., Mol. Gen. Genet 206:192–199 (1987); Pythoud et al., Bio/Technology 5:1323–1327 (1987); De Block, Plant Physiol. 93:1110–1116 (1990); Brasileiro et al., Plant Mol. Bio 17:441–452 (1991); Brasileiro et al., Transgenic Res. 1:133–141 (1992); Howe et al., Woody Plant Biotech., Plenum Press, New York, pp.283–294 (1991); Klopfenstein et al., Can. J. For. Res. 21:1321–1328 (1991); Leple et al., Plant Cell Reports 11:137–141 (1992); and Nilsson et al. Transgenic Res. 1:209–220 (1992).

C. Color Alteration and Lignin Structure

The results of the transformation can be confirmed with conventional PCR and Southern analysis.

The present invention alters the natural wood color of woody plants. In aspen, the natural white/yellow color of the wood is altered to a brownish-red. The appearance of the wood color in aspen is achievable in both a solid and spotted appearance and is stable over time. Furthermore, the altered color of the wood appears in plants that are vegetatively propagated from the original transgenic plant. It should also be noted that with the present invention, the alteration of the natural color in the woody plants is not linked to any threshold increase or decrease in OMT activity.

The transformation of woody plants with a homologous OMT gene also alters the structure of lignin since the OMT gene is a part of the lignin synthesis pathway. For example, in aspen, due to cosuppression, the syringyl units decrease thus altering the structure of the lignin. The altered lignin will aid in the more efficient pulping of the wood of the transgenic plants.

We claim:

1. A method for altering the wood color of a woody plant comprising incorporating into the genome of the woody plant a nucleotide sequence encoding the endogenous full-length enzyme O-methyltransferase in the sense orientation such that when the nucleotide sequence is expressed in the woody plant, the wood color of the woody plant is altered from the natural color.

2. A method for altering the natural wood color of a woody plant as set forth in claim 1 wherein the color of the altered wood is reddish-brown.

3. A method for altering the natural wood color of a woody plant as set forth in claim 1 wherein the nucleotide sequence is incorporated in the genome of the woody plant by transformation.

4. A method for altering the natural wood color of a woody plant as set forth in claim 3 wherein the transformation includes the use of an Agrobacterium transfer vector.

5. A method for altering the natural wood color of a woody plant as set forth in claim 1 wherein the nucleotide sequence is a cloned cDNA sequence of O-methyltransferase.

6. A method for altering the natural wood color of a woody plant as set forth in claim 1 wherein the nucleotide sequence includes a gene promoter sequence.

7. A method for altering the natural wood color of a woody plant as set forth in claim 6 wherein the gene promoter sequence includes CaMV35S.

8. A method for altering the natural wood color of a woody plant as set forth in claim 1 wherein when the nucleotide sequence is expressed in the woody plant, the structure of the lignin of the woody plant is altered.

9. A method for altering the natural wood color of a woody plant as set forth in claim 1 wherein the woody plant is of the genus Populus.

10. A woody plant having the color of its wood altered through the incorporation into the genome of the woody plant a nucleotide sequence encoding the endogenous full-length enzyme O-methyltransferase in the sense orientation.

11. A woody plant as set forth in claim 10 wherein the color of the altered wood is reddish-brown.

12. A woody plant as set forth in claim 10 wherein the nucleotide sequence is incorporated in the genome of the woody plant by transformation.

13. A woody plant as set forth in claim 12 wherein the transformation includes the use of an Agrobacterium transfer vector.

14. A woody plant as set forth in claim 10 wherein the nucleotide sequence is derived from cloned cDNA of O-methyltransferase.

15. A woody plant as set forth in claim 10 wherein the nucleotide sequence includes a gene promoter sequence.

16. A woody plant as set forth in claim 15 wherein the gene promoter sequence includes CaMV35S.

17. A woody plant as set forth in claim 10 wherein when the nucleotide sequence is expressed in the woody plant, the structure of the lignin of the woody plant is altered.

18. A woody plant as set forth in claim 10 wherein the woody plant is of the genus Populus.

19. A recombinant DNA comprising a gene promoter sequence, a gene terminator, and an interposed region comprising a nucleotide sequence encoding the endogenous full-length enzyme O-methyltransferase in the sense orientation such that when the nucleotide sequence is expressed in the woody plant, the wood color of the woody plant is altered from its natural color.

20. A recombinant DNA as set forth in claim 19 wherein the gene promoter sequence includes CaMV35S.

21. A recombinant DNA as set forth in claim 19 and further when the nucleotide sequence is expressed in the woody plant, the structure of the lignin of the woody plant is altered.

22. A method for altering the wood color of a plant of the genus Populous comprising incorporating into the genome of the plant through transformation a nucleotide sequence encoding the endogenous full-length enzyme O-methyltransferase in the sense orientation such that when the nucleotide sequence is expressed in the plant, the wood color of the plant is altered from its natural color.

23. A method for altering the wood color of a plant of the genus Populus as set forth in claim 22 wherein the color of the altered wood is reddish-brown.

24. A method for altering the wood color of a plant of the genus Populus as set forth in claim 22 wherein the transformation includes the use of an Agrobacterium transfer vector.

25. A method for altering the wood color of a plant of the genus Populus as set forth in claim 22 wherein the nucleotide sequence includes a cloned cDNA sequence of O-methyltransferase.

26. A method for altering the wood color of a plant of the genus Populus as set forth in claim 22 wherein the nucleotide sequence includes a gene promoter sequence.

27. A method for altering the wood color of a plant of the genus Populus as set forth in claim 26 wherein the gene promoter sequence includes CaMV35S.

28. A method for altering the wood color of a plant of the genus Populus as set forth in claim 22 wherein when the nucleotide sequence is expressed in the woody plant, the structure of the lignin of the plant is altered.

29. A woody plant of the genus Populus having the natural color of its wood altered through the incorporation into the genome of the woody plant a nucleotide sequence encoding the endogenous full-length enzyme O-methyltransferase in the sense orientation.

30. A woody plant of the genus Populus as set forth in claim 29 wherein the nucleotide sequence includes a CaMV35S gene promoter sequence.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

(i) SEQUENCE CHARACTERISTICS:
  (A) LENGTH: 1503 base pairs
  (B) TYPE: nucleic acid
  (C) STRANDEDNESS: double
  (D) TOPOLOGY: linear (ii) MOLECULE TYPE: cDNA to mRNA (iii) HYPOTHETICAL: no (iv) ANTI-SENSE: no (vi) ORIGINAL SOURCE:
  (A) ORGANISM: Populus Tremuloides
  (D) DEVELOPMENTAL STAGE: four year old sapling
       undergoing lignification in summer
  (F) TISSUE TYPE: secondary xylem (vii) IMMEDIATE SOURCE:
  (A) LIBRARY: cDNA to total mRNA
  (B) CLONE: PtOMT1

(xi) SEQUENCE DESCRIPTION:SEQ ID NO:1:

```
TCACTTCCTT TCCTTACACC TTCTTCAACC TTTTGTTTCC TTGTAGAATT CAATCTCGAT    60

CAAG ATG GGT TCA ACA GGT GAA ACT CAG ATG ACT CCA ACT CAG GTA        106
     Met Gly Ser Thr Gly Glu Thr Gln Met Thr Pro Thr Gln Val
     1           5                   10

TCA GAT GAA GAG GCA CAC CTC TTT GCC ATG CAA CTA GCC AGT GCT TCA     154
Ser Asp Glu Glu Ala His Leu Phe Ala Met Gln Leu Ala Ser Ala Ser
15           20                  25                  30

GTT CTA CCA ATG ATC CTC AAA ACA GCC ATT GAA CTC GAC CTT CTT GAA     202
Val Leu Pro Met Ile Leu Lys Thr Ala Ile Glu Leu Asp Leu Leu Glu
             35                  40                  45

ATC ATG GCT AAA GCT GGC CCT GGT GCT TTC TTG TCC ACA TCT GAG ATA     250
Ile Met Ala Lys Ala Gly Pro Gly Ala Phe Leu Ser Thr Ser Glu Ile
             50                  55                  60

GCT TCT CAC CTC CCT ACC AAA AAC CCT GAT GCG CCT GTC ATG TTA GAC     298
Ala Ser Mis Leu Pro Thr Lys Asn Pro Asp Ala Pro Val Met Leu Asp
         65                  70                  75

CGT ATC CTG CGC CTC CTG GCT AGC TAC TCC ATT CTT ACC TGC TCT CTG     346
Arg Ile Leu Arg Leu Leu Ala Ser Tyr Ser Ile Leu Thr Cys Ser Leu
     80                  85                  90

AAA GAT CTT CCT GAT GGG AAG GTT GAG AGA CTG TAT GGC CTC GCT CCT     394
Lys Asp leu Pro Asp Gly Lys Val Glu Arg Leu Tyr Gly Leu Ala Pro
95              100                 105                 110

GTT TGT AAA TTC TTG ACC AAG AAC GAG GAC GGT GTC TCT GTC AGC CCT     442
Val Cys Lys Phe Leu Thr Lys Asn Glu Asp Gly Val Ser Val Ser Pro
                115                 120                 125

CTC TGT CTC ATG AAC CAG GAC AAG GTC CTC ATG GAA AGC TGG TAT TAT     490
Leu Cys Leu Met Asn Gln Asp Lys Val Leu Met Glu Ser Trp Tyr Tyr
            130                 135                 140

TTG AAA GAT GCA ATT CTT GAT GGA GGA ATT CCA TTT AAC AAG GCC TAT     538
Leu Lys Asp Ala Ile Leu Asp Gly Gly Ile Pro Phe Asn Lys Ala Tyr
        145                 150                 155

GGG ATG ACT GCA TTT GAA TAT CAT GGC ACG GAT CCA AGA TTC AAC AAG     586
Gly Met Thr Ala Phe Glu Tyr His Gly Thr Asp Pro Arg Phe Asn Lys
    160                 165                 170

GTC TTC AAC AAG GGA ATG TCT GAC CAC TCT ACC ATT ACC ATG AAG AAG     634
Val Phe Asn Lys Gly Met Ser Asp His Ser Thr Ile Thr Met Lys Lys
175                 180                 185                 190

ATT CTT GAG ACC TAC AAA GGC TTT GAA GGC CTC ACG TCC TTG GTG GAT     682
Ile Leu Glu Thr Tyr Lys Gly Phe Glu Gly Leu Thr Ser Leu Val Asp
                195                 200                 205
```

| | | | | | | | | | | | | | | | | |
|---|---|---|---|---|---|---|---|---|---|---|---|---|---|---|---|---|
| GTT | GGT | GGT | GGG | ACT | GGA | CCC | GTC | GTT | AAC | ACC | ATC | GTC | TCT | AAA | TAC | 730 |
| Val | Gly | Gly | Gly | Thr | Gly | Ala | Val | Val | Asn | Thr | Ile | Val | Ser | Lys | Tyr | |
| | | | 210 | | | | | 215 | | | | | 220 | | | |
| CCT | TCA | ATC | AAG | GGC | ATT | AAC | TTC | GAT | CTG | CCC | CAC | GTC | ATT | GAG | GAT | 778 |
| Pro | Ser | Ile | Lys | Gly | Ile | Asn | Phe | Asp | Leu | Pro | His | Val | Ile | Glu | Asp | |
| | | 225 | | | | | 230 | | | | | 235 | | | | |
| GCC | CCA | TCT | TAT | CCC | GGA | GTG | GAG | CAT | GTT | GGT | GGC | GAC | ATG | TTT | GTT | 826 |
| Ala | Pro | Ser | Tyr | Pro | Gly | Val | Glu | His | Val | Gly | Gly | Asp | Met | Phe | Val | |
| | | 240 | | | | | 245 | | | | | 250 | | | | |
| AGT | GTG | CCC | AAA | GCA | GAT | GCC | GTT | TTC | ATG | AAG | TGG | ATA | TGC | CAT | GAT | 874 |
| Ser | Val | Pro | Lys | Ala | Asp | Ala | Val | Phe | Met | Lys | Trp | Ile | Cys | His | Asp | |
| 255 | | | | | 260 | | | | | 265 | | | | | 270 | |
| TGG | AGC | GAC | GCC | CAC | TGC | TTA | AAA | TTC | TTG | AAG | AAT | TGC | TAT | GAC | GCG | 922 |
| Trp | Ser | Asp | Ala | His | Cys | Leu | Lys | Phe | Leu | Lys | Asn | Cys | Tyr | Asp | Ala | |
| | | | | 275 | | | | | 280 | | | | | 285 | | |
| TTG | CCG | GAA | AAC | GGC | AAG | GTG | ATA | CTT | GTT | GAG | TGC | ATT | CTT | CCC | GTG | 970 |
| Leu | Pro | Glu | Asn | Gly | Lys | Val | Ile | Leu | Val | Glu | Cys | Ile | Leu | Pro | Val | |
| | | | | 290 | | | | | 295 | | | | | 300 | | |
| GCT | CCT | GAC | ACA | AGC | CTT | GCC | ACC | AAG | GGA | GTC | GTG | CAC | GTT | GAT | GTC | 1018 |
| Ala | Pro | Asp | Thr | Ser | Leu | Ala | Thr | Lys | Gly | Val | Val | His | Val | Asp | Val | |
| | | | 305 | | | | | 310 | | | | | 315 | | | |
| ATC | ATG | CTG | GCG | CAC | AAC | CCC | GGT | GGG | AAA | GAG | AGG | ACC | GAG | AAG | GAA | 1066 |
| Ile | Met | Leu | Ala | His | Asn | Pro | Gly | Gly | Lys | Glu | Arg | Thr | Glu | Lys | Glu | |
| | | 320 | | | | | 325 | | | | | 330 | | | | |
| TTT | GAG | GGC | TTA | GCT | AAG | GGA | GCT | GGC | TTC | CAA | GGT | TTT | GAA | GTA | ATG | 1114 |
| Phe | Glu | Gly | Leu | Ala | Lys | Gly | Ala | Gly | Phe | Gln | Gly | Phe | Glu | Val | Met | |
| 335 | | | | | 340 | | | | | 345 | | | | | 350 | |
| TGC | TGT | GCA | TTC | AAC | ACA | CAT | GTC | ATT | GAA | TTC | CGC | AAG | AAG | GCC | | 1159 |
| Cys | Cys | Ala | Phe | Asn | Thr | His | Val | Ile | Glu | Phe | Arg | Lys | Lys | Ala | | |
| | | | | 355 | | | | | 360 | | | | | 365 | | |

| | | | | |
|---|---|---|---|---|
| TAAGGCCCAT | GTCCAAGCTC | CAAGTTACTT | GGGGTTTTGC | AGACAACGTT GCTGCTGTCT | 1219 |
| CTGCGTTTGA | TGTTTCTGAT | TGCTTTTTTT | TATACGAGGA | GTAGCTATCT CTTATGAAAC | 1279 |
| ATGTAAGGAT | AAGATTGCGT | TTTGTATGCC | TGATTTTCTC | AAATAACTTC ACTGCCTCCC | 1339 |
| TCAAAATTCT | TAATACATGT | GAAAAGATTT | CCTATTGGCC | TTCTGCTTCA AACAGTAAAG | 1399 |
| ACTTCTGTAA | CGGAAAAGAA | AGCAATTCAT | GATGTATGTA | TCTTGCAAGA TTATGAGTAT | 1459 |
| TGTTCTAAGC | ATTAAGTGAT | TGTTCAAAAA | AAAAAAAAA | AAAA | 1503 |

( 2 ) INFORMATION FOR SEQ ID NO:2:

( i ) SEQUENCE CHARACTERISTICS:
    ( A ) LENGTH: 365 amino acids
    ( B ) TYPE: amino acid
    ( D ) TOPOLOGY: linear ( i i ) MOLECULE TYPE:
    ( A ) DESCRIPTION: protein ( i i i ) HYPOTHETICAL: no ( x i ) SEQUENCE DESCRIPTION:SEQ ID NO:2:

| | | | | | | | | | | | | | | | |
|---|---|---|---|---|---|---|---|---|---|---|---|---|---|---|---|
| Met | Gly | Ser | Thr | Gly | Glu | Thr | Gln | Met | Thr | Pro | Thr | Gln | Val | Ser | Asp |
| 1 | | | | 5 | | | | | 10 | | | | | 15 | |
| Glu | Glu | Ala | His | Leu | Phe | Ala | Met | Gln | Leu | Ala | Ser | Ala | Ser | Val | Leu |
| | | | 20 | | | | | 25 | | | | | 30 | | |
| Pro | Met | Ile | Leu | Lys | Thr | Ala | Ile | Glu | Leu | Asp | Leu | Leu | Glu | Ile | Met |
| | | | 35 | | | | | 40 | | | | | 45 | | |
| Ala | Lys | Ala | Gly | Pro | Gly | Ala | Phe | Leu | Ser | Thr | Ser | Glu | Ile | Ala | Ser |
| | | 50 | | | | | 55 | | | | | 60 | | | |
| His | Leu | Pro | Thr | Lys | Asn | Pro | Asp | Ala | Pro | Val | Met | Leu | Asp | Arg | Ile |
| 65 | | | | | 70 | | | | | 75 | | | | | 80 |

-continued

| | | | | | | | | | | | | | | |
|---|---|---|---|---|---|---|---|---|---|---|---|---|---|---|
| Leu | Arg | Leu | Leu | Ala 85 | Ser | Tyr | Ser | Ile | Leu 90 | Thr | Cys | Ser | Leu | Lys 95 | Asp |
| Leu | Pro | Asp | Gly 100 | Lys | Val | Glu | Arg | Leu 105 | Tyr | Gly | Leu | Ala | Pro 110 | Val | Cys |
| Lys | Phe | Leu 115 | Thr | Lys | Asn | Glu | Asp 120 | Gly | Val | Ser | Val | Ser 125 | Pro | Leu | Cys |
| Leu | Met 130 | Asn | Gln | Asp | Lys | Val 135 | Leu | Met | Glu | Ser | Trp 140 | Tyr | Tyr | Leu | Lys |
| Asp 145 | Ala | Ile | Leu | Asp | Gly 150 | Gly | Ile | Pro | Phe | Asn 155 | Lys | Ala | Tyr | Gly | Met 160 |
| Thr | Ala | Phe | Glu | Tyr 165 | His | Gly | Thr | Asp | Pro 170 | Arg | Phe | Asn | Lys | Val 175 | Phe |
| Asn | Lys | Gly | Met 180 | Ser | Asp | His | Ser | Thr 185 | Ile | Thr | Met | Lys | Lys 190 | Ile | Leu |
| Glu | Thr | Tyr 195 | Lys | Gly | Phe | Glu | Gly 200 | Leu | Thr | Ser | Leu | Val 205 | Asp | Val | Gly |
| Gly | Gly 210 | Thr | Gly | Ala | Val | Val 215 | Asn | Thr | Ile | Val | Ser 220 | Lys | Tyr | Pro | Ser |
| Ile 225 | Lys | Gly | Ile | Asn | Phe 230 | Asp | Leu | Pro | His | Val 235 | Ile | Glu | Asp | Ala | Pro 240 |
| Ser | Tyr | Pro | Gly | Val 245 | Glu | His | Val | Gly | Gly 250 | Asp | Met | Phe | Val | Ser 255 | Val |
| Pro | Lys | Ala | Asp 260 | Ala | Val | Phe | Met | Lys 265 | Trp | Ile | Cys | His | Asp 270 | Trp | Ser |
| Asp | Ala | His 275 | Cys | Leu | Lys | Phe | Leu 280 | Lys | Asn | Cys | Tyr | Asp 285 | Ala | Leu | Pro |
| Glu | Asn 290 | Gly | Lys | Val | Ile | Leu 295 | Val | Glu | Cys | Ile | Leu 300 | Pro | Val | Ala | Pro |
| Asp 305 | Thr | Ser | Leu | Ala | Thr 310 | Lys | Gly | Val | Val | His 315 | Val | Asp | Val | Ile | Met 320 |
| Leu | Ala | His | Asn | Pro 325 | Gly | Gly | Lys | Glu | Arg 330 | Thr | Glu | Lys | Glu | Phe 335 | Glu |
| Gly | Leu | Ala | Lys 340 | Gly | Ala | Gly | Phe | Gln 345 | Gly | Phe | Glu | Val | Met 350 | Cys | Cys |
| Ala | Phe | Asn 355 | Thr | His | Val | Ile | Glu 360 | Phe | Arg | Lys | Lys | Ala 365 | | | |